United States Patent [19]
Murry et al.

[11] Patent Number: 6,114,123
[45] Date of Patent: Sep. 5, 2000

[54] LIPOCALIN FAMILY PROTEIN

[75] Inventors: Lynn E. Murry, Portola Valley; Tom Y. Tang, San Jose; Mariah R. Baughn, San Leandro, all of Calif.

[73] Assignee: Incyte Pharmaceuticals, Inc., Palo Alto, Calif.

[21] Appl. No.: 09/332,934

[22] Filed: Jun. 14, 1999

[51] Int. Cl.[7] ............... C12Q 1/68; C12N 15/12; C12N 15/63

[52] U.S. Cl. ............... 435/6; 530/300; 530/350; 536/23.1; 435/320.1; 435/325; 435/69.1; 435/252.3

[58] Field of Search ............... 435/69.1, 252.3, 435/320.1, 325, 6; 530/350; 536/23.1

[56] References Cited

U.S. PATENT DOCUMENTS 5,869,250  2/1999  Cheng ............... 435/6

OTHER PUBLICATIONS

Bartsch S et al, "Cloning and expression of human neutrophil lipocalin cDNA derived from bone marrow and ovarian cancer cells", FEBS Letters, Jan. 9, 1995, 357(3):255–259.

Deissler, H et al, "Purification of nuclear proteins from human HeLa cells that bind specifically to the unstable tandem repeat (CGG)n in the human FMR1 gene", J of Biol Chem, Feb. 23, 1996, 271(8): 4327–4334.

Flower, D.R., The Lipocalin protein family: structure and function, *Biochem. J.*, 318:1–14, (1996).

Flower, D.R., The lipocalin protein family: a role in cell regulation, *FEBS Letter*, 354:7–11, (1994).

Rowen, L., et al., (Direct Submission), GenBank Sequence Database (Accession AAC82478), National Center for Biotechnology Information, National Library of Medicine, Bethesda, Maryland, 20894 (GI 3941735).

Xu, N., et al., (Direct Submission), GenBank Sequence Database (Accession AF118393), National Center for Biotechnology Information, National Library of Medicine, Bethesda, Maryland, 20894 (GI 4206178).

Rowen, L., et al., (Direct Submission), GenBank Sequence Database (Accession AAD18084), National Center for Biotechnology Information, National Library of Medicine, Bethesda, Maryland, 20894 (GI 4337108).

Drayna, D., et al., (Direct Submission), GenBank Sequence Database (Accession NP_001638), National Center for Biotechnology Information, National Library of Medicine, Bethesda, Maryland, 20894 (GI 4502163).

Girotti, M., et al., (Direct Submission), GenBank Sequence Database (Accession P06911), National Center for Biotechnology Information, National Library of Medicine, Bethesda, Maryland, 20894 (GI 113824).

*Primary Examiner*—John S. Brusca
*Assistant Examiner*—Stephen Siu
*Attorney, Agent, or Firm*—Incyte Pharmaceuticals, Inc.; Christopher Turner

[57] ABSTRACT

The invention provide a mammalian nucleic acid molecule and fragments thereof. It also provides for the use of the mammalian nucleic acid molecule for the characterization, diagnosis, evaluation, treatment, or prevention of conditions, diseases and disorders associated with gene expression and for the production of a model system. The invention additionally provides expression vectors and host cells for the production of the protein encoded by the mammalian nucleic acid molecule.

13 Claims, 5 Drawing Sheets

```
                                    10            19         28          37         46          55
5' GCAG CCA GTA GGG GAG AGA GCA GTT AAG GCA CAC AGA GCA CCA CCC TCC TGC
                                                                              64           73         82          91        100         109
CTG AAG ATG TTC CAC CAA ATT TGG GCA GCT CTG TAC TTC TAT GGT ATT ATC
        M   F   H   Q   I   W   A   A   L   Y   F   Y   G   I   I
                   118         127        136         145        154         163
CTT AAC TCC ATC TAC CAG TGC CCT GAG CAC AGT CAA CTG ACA CTG GGC GTG
 L   N   S   I   Y   Q   C   P   E   H   S   Q   L   T   L   G   V
                   172         181        190         199        208         217
GAT GGG AAG GAG TTC CCA GAG GTC CAC TTG GGC TAC TTT ATC GAC AAC ATT GCA GGG
 D   G   K   E   F   P   E   V   H   L   G   Y   F   I   D   N   I   A   G
                   226         235        244         253        262         271
GCA GCT CCC ACC AAG GAG GAG TTG GCA ACT TTT GAC CCT GTG CAC CTT CGT GCT ACC GTC
 A   A   P   T   K   E   E   L   A   T   F   D   P   V   H   L   R   A   T   V
                   280         289        298         307        316         325
TTC AAT ATG GCT GCT GGC TCT GCC CCG ATG CAG CTC CAC CTC GAC AAC ATT
 F   N   M   A   A   G   S   A   P   M   Q   L   H   L   D   N   I
                   334         343        352         361        370         379
CGC ATG AAA GAT GGG CTC TGT GTG CCC CGG AAA TGG ATC TAC CAC CTG ACT GAA
 R   M   K   D   G   L   C   V   P   R   K   W   I   Y   H   L   T   E
```

FIGURE 1A

```
                388            397            406            415            424            433
GGG AGC ACA GAT CTC AGA ACT GAA GGC CGC CCT GAC ATG AAG ACT GAG CTC TTT
 G   S   T   D   L   R   T   E   G   R   P   D   M   K   T   E   L   F
     442            451            460            469            478            487
TCC AGC TCA TGC CCA GGT GGA ATC ATG CTG AAT GAG ACA GGC CAG GGT TAC CAG
 S   S   S   C   P   G   G   I   M   L   N   E   T   G   Q   G   Y   Q
     496            505            514            523            532            541
CGC TTT CTC TAC AAT CGC TCA CCA CAT CCT CCC GAA AAG TGT GTG GAG GAA
 R   F   L   Y   N   R   S   P   H   P   P   E   K   C   V   E   E
     550            559            568            577            586            595
TTC AAG TCC CTG ACT GAG CTG TGC CTG GAC TCC AAA GCC TTC TTA ACT CCT AGG
 F   K   S   L   T   E   L   C   L   D   S   K   A   F   L   T   P   R
     604            613            622            631            640            649
AAT CAA GAG GCC TGT AAT CGC TCC AAT AAC TGA CCT GTA ACT TCA TCT AAG TCC
 N   Q   E   A   C   N   R   S   N   N   *
     658            667            676            685            694            703
CCA GAT GGG TAC AAT GGG AGC TGA GTT GTT GGA AGG AGA NGC TGG AGA CTT CCA
     712            721            730            739            748            757
GCT CCA GCT CCC ACT CAA GAT AAT AAA GAT AAT TTT TCA ATC CTC AAA NAN AAA  3'
```

FIGURE 1B

```
                                      11   20            29            38            47            56
5' GGGGG CTG GAG GCA GAG CAG ACT GGG CAT GCC AGC AGA GAA CAG TTA AGG TAG AGG 65            74            83            92           101           110
   TCC CCA GAA CCG CAC AGC GCC AGG TCT CCT CCC AAG ATG TTC CAC CAA GTC TGG
                                                                   M   F   H   Q   V   W 119           128           137           146           155           164
   GCA GCG CTG CTC TAT CTC TTT AAC TCC ATG AAT CAG TGC CCT
   A   A   L   L   Y   L   F   N   S   M   N   Q   C   P 173           182           191           200           209           218
   GAG CAC AGT CAA CTA ACG ACG CTG GGA ATG GAC AAA GAG CCA GAG CCC
   E   H   S   Q   L   T   T   L   G   M   D   K   E   P   E   P 227           236           245           254           263           272
   CAC CTG GGC CTG TGG TAC TTT ATC GCT GGA GCG CCC ACC ATG GAA GAG TTG
   H   L   G   L   W   Y   F   I   A   G   A   P   T   M   E   E   L 281           290           299           308           317           326
   GCA ACT TTT GAC CAG GTA GAC AAT ATT GTC TTC AAC ATG GCC GCC TCT GCC
   A   T   F   D   Q   V   D   N   I   V   F   N   M   A   A   S   A 335           344           353           362           371           380
   CCA AGG CAG CTC CAG CTT CGC GCT ACC ATT CGC ACG AAA AAC GGG GTC TGT GTG
   P   R   Q   L   Q   L   R   A   T   I   R   T   K   N   G   V   C   V
```

FIGURE 2A

```
      389                 398                 407                 416                 425              434
CCC CGG AAA TGG ACG TAC CAC TTG ACT GAA GGG AAA GGA AAC ACG GAA CTC AGA
 P   R   K   W   T   Y   H   L   T   E   G   K   G   N   T   E   L   R 443                 452                 461                 470                 479              488
ACT GAA GGG CGC CCA GAC ATG AAA ACA GAC CTC TTC TCC ATC TCA TGC CCA GGA
 T   E   G   R   P   D   M   K   T   D   L   F   S   I   S   C   P   G 497                 506                 515                 524                 533              542
GGA ATC ATG CTG AAA GAG ACG GGG TAC CAG GGG TAC CAG CGT TTC CTC CTC TAC AAC
 G   I   M   L   K   E   T   G   Q   G   Y   Q   R   F   L   L   Y   N 551                 560                 569                 578                 587              596
CGA TCG CCA CAC CCT CCA GAG GAG TGT GTG ACT GTG GAA TTC CAG TCT CTG ACA TCC
 R   S   P   H   P   P   E   E   C   V   T   V   E   F   Q   S   L   T   S 605                 614                 623                 632                 641              650
TGC TTG GAC TTC AAA GCC TTT TTA GTG ACT CCC AGG AAT CAA GAG GCC TGC CCA
 C   L   D   F   K   A   F   L   V   T   P   R   N   Q   E   A   C   P 659                 668                 677                 686                 695              704
CTG TCC AGC AAG TGA CCC GTG ACT CCA CCT GTG TCC TGG ACA GGC ACG ATA GGA
 L   S   S   K 713                 722                 731                 740                 749              758
GCT GAG CTC TGA GGG GAG AAG CCA GAG ACT CCC GCT CCC TCT CAT GGA TAA TAA 767                 776
AGA TGA ATT GTC AAT CCT C 3'
```

LIPOCALIN FAMILY PROTEIN

FIELD OF THE INVENTION

This invention relates to nucleic acid molecules and amino acid sequences of a new mammalian protein and to their use in the characterization, diagnosis, prevention, and treatment of conditions such as cell proliferative and immune disorders.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical and structural features and modulate the same general activity. Comparisons of human gene sequences with those from other organisms where structure and/or function are known allow researchers to draw analogies and to develop model systems for testing diagnostic and therapeutic agents for human conditions, diseases, and disorders.

The lipocalins are a family of extracellular ligand-binding proteins which bind and transport small hydrophobic molecules. Lipocalins function in a variety of processes including nutrient transport, cell growth regulation, immune response, and prostaglandin synthesis.

Members of the lipocalin family display unusually low levels of overall sequence conservation. Pairwise sequence identity often falls below 20%, the threshold for reliable alignment. Sequence similarity between family members is limited to conserved cysteines which form disulfide bonds and three motifs which form a juxtaposed cluster that functions as a target cell recognition site. The lipocalins share an eight stranded, anti-parallel beta-sheet which folds back on itself to form a continuously hydrogen-bonded beta-barrel. The pocket formed by the barrel functions as an internal ligand binding site. Seven loops (L1 to L7) form short beta-hairpins, except loop L1 which is a large omega loop that forms a lid to partially close the internal ligand-binding site (Flower (1996) Biochem. J. 318:1–14).

Lipocalins are important transport molecules. Each lipocalin associates with a particular ligand and delivers that ligand to appropriate target sites within the organism. Retinol-binding protein (RBP), one of the best characterized lipocalins, transports retinol from stores within the liver to target tissues. Apolipoprotein D (apo D), a component of high density lipoproteins (HDLs) and low density lipoproteins (LDLs), functions in the targeted collection and delivery of cholesterol throughout the body. Lipocalins also are involved in cell regulatory processes. Apo D, which is identical to gross-cystic-disease-fluid protein (GCDFP)-24, is a progesterone/pregnenolone-binding protein expressed at high levels in breast cyst fluid. Secretion of apo D in certain human breast cancer cell lines is accompanied by reduced cell proliferation and progression of cells to a more differentiated phenotype. Similarly, apo D and another lipocalin, $\alpha_1$-acid glycoprotein (AGP), are involved in nerve cell regeneration. AGP is also involved in anti-inflammatory and immunosuppressive activities. AGP is one of the positive acute-phase proteins (APP); circulating levels of AGP increase in response to stress and inflammatory stimulation. AGP accumulates at sites of inflammation where it inhibits platelet and neutrophil activation and inhibits phagocytosis. The immunomodulatory properties of AGP are due to glycosylation. AGP is 40% carbohydrate, making it unusually acidic and soluble. The glycosylation pattern of AGP changes during acute-phase response, and deglycosylated AGP has no immunosuppressive activity (Flower (1994) FEBS Lett. 354:7–11; Flower, supra).

Lipocalins are used as diagnostic and prognostic markers in a variety of disease states. The plasma level of AGP is monitored during pregnancy and in diagnosis and prognosis of conditions including cancer chemotherapy, renal disfunction, myocardial infarction, arthritis, and multiple sclerosis. RBP is used clinically as a marker of tubular reabsorption in the kidney, and apo D is a marker in gross cystic breast disease (Flower (1996) supra).

The discovery of mammalian nucleic acid molecules encoding a lipocalin family protein provides new compositions which are useful in the characterization, diagnosis, prevention, and treatment of cell proliferative and immune disorders.

SUMMARY OF THE INVENTION

The invention is based on the discovery of a substantially purified mammalian nucleic acid molecule encoding a mammalian protein, lipocalin family protein (LCFP), which satisfies a need in the art by providing compositions useful in the characterization, diagnosis, prevention, and treatment of conditions such as cell proliferative and immune disorders.

The invention provides isolated and purified human and rat nucleic acid molecules comprising SEQ ID NOs:1 and 10, and fragments thereof SEQ ID NOs:3–9, encoding the mammalian protein comprising amino acid sequences of SEQ ID NOs:2 and 11, or portions thereof.

The invention further provides a probe which hybridizes under high stringency conditions to the mammalian nucleic acid molecule or fragments thereof. The invention also provides isolated and purified nucleic acid molecules which are complementary to the nucleic acid molecules of SEQ ID NOs:1 and 3–10. In one aspect, the probe is a single stranded complementary RNA or DNA molecule.

The invention further provides a method for detecting a nucleic acid molecule in a sample, the method comprising the steps of hybridizing a probe to at least one nucleic acid molecule of a sample, forming a hybridization complex; and detecting the hybridization complex, wherein the presence of the hybridization complex indicates the presence of the nucleic acid molecule in the sample. In one aspect, the method further comprises amplifying the nucleic acid molecule prior to hybridization. The nucleic acid molecule or a fragment thereof may comprise either an element or a target on a microarray.

The invention also provides a method for using a nucleic acid molecule or a fragment thereof to screen a library of molecules to identify at least one ligand which specifically binds the nucleic acid molecule, the method comprising combining the nucleic acid molecule with a library of molecules under conditions allowing specific binding, and detecting specific binding, thereby identifying a ligand which specifically binds the nucleic acid molecule. Such libraries include DNA and RNA molecules, peptides, PNAs, proteins, and the like. In an analogous method, the nucleic acid molecule or a fragment thereof is used to purify a ligand.

The invention also provides an expression vector containing at least a fragment of the nucleic acid molecule. In another aspect, the expression vector is contained within a host cell. The invention further provides a method for producing a protein, the method comprising the steps of culturing the host cell under conditions for the expression of the protein and recovering the protein from the host cell culture.

The invention also provides a substantially purified mammalian lipocalin family protein or a portion thereof. The invention further provides isolated and purified proteins having the amino acid sequences of SEQ ID NOs:2 and 11. Additionally, the invention provides a pharmaceutical composition comprising a substantially purified mammalian protein or a portion thereof in conjunction with a pharmaceutical carrier.

The invention further provides a method for using at least a portion of the mammalian protein to produce antibodies. The invention also provides a method for using a mammalian protein or a portion thereof to screen a library of molecules to identify at least one ligand which specifically binds the protein, the method comprising combining the protein with the library of molecules under conditions allowing specific binding, and detecting specific binding, thereby identifying a ligand which specifically binds the protein. Such libraries include DNA and RNA molecules, peptides, agonists, antagonists, antibodies, immunoglobulins, drug compounds, pharmaceutical agents, and other ligands. In one aspect, the ligand identified using the method modulates the activity of the mammalian protein. In an analogous method, the protein or a portion thereof is used to purify a ligand. The method involves combining the mammalian protein or a portion thereof with a sample under conditions to allow specific binding, detecting specific binding between the protein and ligand, recovering the bound protein, and separating the protein from the ligand to obtain purified ligand.

The invention further provides a method for inserting a marker gene into the genomic DNA of a mammal to disrupt the expression of the natural mammalian nucleic acid molecule. The invention also provides a method for using the mammalian nucleic acid molecule to produce a mammalian model system, the method comprising constructing a vector containing the mammalian nucleic acid molecule; introducing the vector into a totipotent mammalian embryonic stem cell; selecting an embryonic stem cell with the vector integrated into genomic DNA; microinjecting the selected cell into a mammalian blastocyst, thereby forming a chimeric blastocyst; transferring the chimeric blastocyst into a pseudopregnant dam, wherein the dam gives birth to a chimeric mammal containing at least one additional copy of mammalian nucleic acid molecule in its germ line; and breeding the chimeric mammal to generate a homozygous mammalian model system.

BRIEF DESCRIPTION OF THE FIGURES

FIGS. 1A and 1B show the human nucleic acid molecule (SEQ ID NO:1) encoding the human amino acid sequence (SEQ ID NO:2) of the mammalian protein. The alignment was produced using MACDNASIS PRO software (Hitachi Software Engineering, South San Francisco Calif.).

FIGS. 2A and 2B show the rat nucleic acid molecule (SEQ ID NO:10) encoding the rat amino acid sequence (SEQ ID NO:11) of the mammalian protein. The alignment was produced using MACDNASIS PRO software (Hitachi Software Engineering).

FIG. 3 demonstrates the chemical and structural similarity among human, 28565127 (SEQ ID NO:2); rat, 700046753 (SEQ ID NO:1); and mouse NG20, g3941735 (SEQ ID NO:12) proteins, produced using the MEGALIGN program (DNASTAR, Madison Wis.).

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"Lipocalin family protein (LCFP)" refers to a substantially purified protein obtained from any mammalian species, including murine, bovine, ovine, porcine, rodent, canine, simian, and preferably the human species, and from any source, whether natural, synthetic, semi-synthetic, or recombinant.

"Biologically active" refers to a protein having structural, immunological, regulatory, or chemical functions of a naturally occurring, recombinant or synthetic molecule "Complementary" refers to the natural hydrogen bonding by base pairing between purines and pyrimidines. For example, the sequence A-C-G-T forms hydrogen bonds with its complements T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a nucleic acid molecule or amino acid sequence. Chemical modifications can include replacement of hydrogen by an alkyl, acyl, or amino group or glycosylation, pegylation, or any similar process which retains or enhances biological activity or lifespan of the molecule or sequence.

"Fragment" refers to an Incyte clone or any part of a nucleic acid molecule which retains a usable, functional characteristic. Useful fragments include oligonucleotides which may be used in hybridization or amplification technologies or in regulation of replication, transcription or translation.

"Hybridization complex" refers to a complex between two nucleic acid molecules by virtue of the formation of hydrogen bonds between purines and pyrimidines.

"Ligand" refers to any molecule, agent, or compound which will bind specifically to a complementary site on a nucleic acid molecule or protein. Such ligands stabilize or modulate the activity of nucleic acid molecules or proteins of the invention and may be composed of at least one of the following: inorganic and organic substances including nucleic acids, proteins, carbohydrates, fats, and lipids.

"Modulates" refers to a change in activity (biological, chemical, or immunological) or lifespan resulting from specific binding between a molecule and either a nucleic acid molecule or a protein.

"Nucleic acid molecule" refers to a nucleic acid, oligonucleotide, nucleotide, polynucleotide or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules to identify molecules which specifically bind to that portion or for the production of antibodies.

"Sample" is used in its broadest sense. A sample containing nucleic acid molecules may comprise a bodily fluid; an extract from a cell, chromosome, organelle, or membrane isolated from a cell; genomic DNA, RNA, or cDNA in solution or bound to a substrate; a cell; a tissue; a tissue print; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

The Invention

The invention is based on the discovery of a new mammalian nucleic acid molecule which encodes a mammalian protein, lipocalin family protein (LCFP), and on the use of the nucleic acid molecule, or fragments thereof, and protein, or portions thereof, as compositions in the characterization, diagnosis, treatment, or prevention of conditions such as cell proliferative and immune disorders.

Nucleic acid molecules encoding the mammalian lipocalin family protein of the present invention were identified by using Blast to annotate unique clones in the ZOOSEQ database (Incyte Pharmaceuticals, Palo Alto Calif.) and assembling the clones with homology to mouse NG20 (SEQ ID NO:12). The clones from various rat liver libraries: 701318182H1, 700046753H1, 701427716T1, and 7006081831H1; SEQ ID NOs:6–9, respectively; were assembled using Phrap into the consensus nucleic acid molecule, SEQ ID NO:10, which encodes the protein having the amino acid sequence of SEQ ID NO:11 (FIGS. 2A and 2B). PFAM confirmed the identity of SEQ ID NO:11 as a lipocalin family protein based on amino acid sequence identity from L148 through C185 of SEQ ID NO:11. In addition, PRINTS identifies two lipocalin signatures in SEQ ID NO:11 from residues E41 through A53 and L148 through F163.

SEQ ID NO:10 was used to identify human lipocalin family nucleic acid molecules in the Incyte LIFESEQ database (Incyte Pharmaceuticals). Incyte clones (libraries) 4069566H1 (KIDNNOT26), 4419443H1 (LIVRDIT02), and 2865127H1 (KIDNNOT20); SEQ ID NOs:3–5, respectively; contributed to the assembly of the consensus sequence, SEQ ID NO:1(FIGS. 1A and 1B). Northern analysis shows expression of this molecule in various libraries, particularly digestive system (67%) and reproductive (17%) tissues. SEQ ID NO:1 has a 67% association with cancerous or proliferating tissues and a 17% association with inflamed, immune responsive, or infected tissues.

The nucleic acid sequences, SEQ ID NO:1, SEQ ID NO:10, and their respective fragments (SEQ ID NOs:3–9) may be used in hybridization and amplification technologies to identify and distinguish among SEQ ID NO:1, SEQ ID NO:10, and similar molecules in a sample. The molecules may be used to mimic human conditions, diseases, or disorders, produce transgenic animal models for these conditions, or to monitor animal toxicology studies, clinical trials, and subject/patient treatment profiles.

Figure 3:
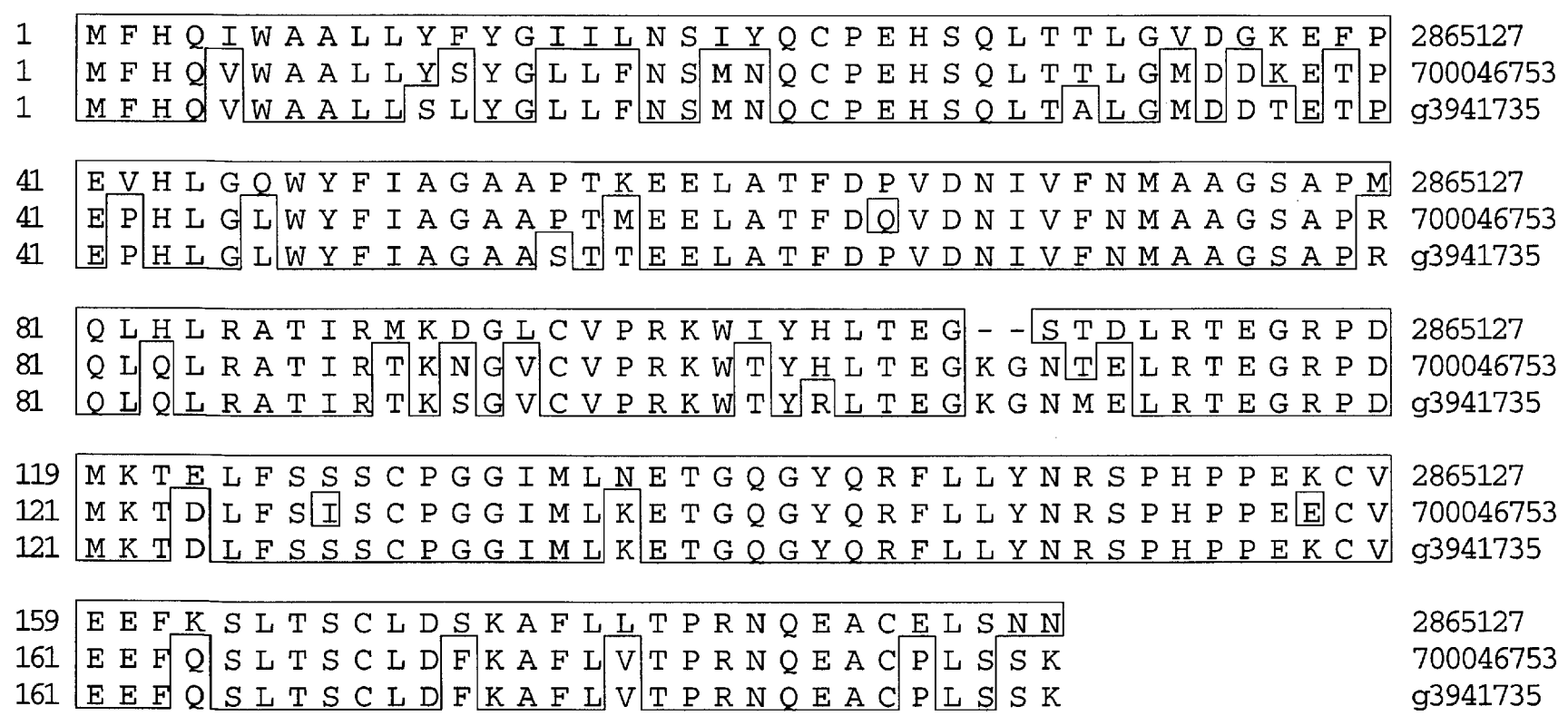

LCFP comprises the amino acid sequences of SEQ ID NO:2, 188 amino acids in length, and of SEQ ID NO:11, 190 amino acids in length. The human protein (SEQ ID NO:2) has a potential N-glycosylation site at N135. The following chemical and structural characterization of the lipocalin family proteins will be based on absolute positions (60 residues per line) shown in FIG. 3. The human, rat and mouse proteins (SEQ ID NOs:2, 11,and 12, respectively) share two casein kinase II phosphorylation sites at residues T56 and S165; two protein kinase C phosphorylation sites at residues T87 and T178; and two lipocalin signatures from residues E41 through A53 and L148 through F163. In addition, the cysteine residues, C23, C95, C130, C159, C169, and C185, essential in lipocalin disulfide bonding, and the proline (P24, P40, P79, P97, P119, P131, P153, P155, P156, and P179), arginine (R85, R89, R98, R114, R118, R145, R151, and R180) and tyrosine (Y13, Y48, Y102, Y143, and Y149) residues important in protein folding and conformation are conserved among the three mammalian species as shown in FIG. 3. SEQ ID NO:2 shares 81.4% similarity with SEQ ID NO:11 and 79.8% similarity with SEQ ID NO:12 (calculated using LASERGENE software, DNASTAR). SEQ ID NOs:2 and 11 are similar in size, 21.3 kDa, and 21.5 kDa, respectively, and isoelectric point, pI of 5.8 and 5.9, respectively (calculated using LASERGENE software, DNASTAR). SEQ ID NO:2 is also of similar length, size, and pI to lipocalin family members human apo D (g4502163, SEQ ID NO:13; 189 amino acids, 21.3 kDa, and pI 5.0, respectively) and rat retinol binding protein (g 113824, SEQ ID NO:14; 188 amino acids, 20.7 kDa, and pI 5.22, respectively). The amino acids of SEQ ID NO:2 from residue H83 to residue W100 are useful for antibody production.

Characterization and Use of the Invention cDNA libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequences were chemically and/or electronically assembled from fragments including Incyte clones and extension and/or shotgun sequences using computer programs such as Phrap (P. Green, University of Washington, Seattle Wash.), GELVIEW Fragment Assembly system (Genetics Computer Group, Madison Wis.), and AUTOASSEMBLER application (Perkin Elmer, Norwalk Conn.).

Sequencing

Methods for sequencing nucleic acids are well known in the art and may be used to practice any of the embodiments of the invention. These methods employ enzymes such as the Klenow fragment of DNA polymerase I, SEQUENASE (USB, Cleveland Ohio), Taq DNA polymerase (Perkin-Elmer), thermostable T7 DNA polymerase (Amersham Pharmacia Biotech, Piscataway N.J.), or combinations of polymerases and proofreading exonucleases such as those found in the ELONGASE amplification system (Life Technologies, Rockville Md.). Preferably, sequence preparation is automated with machines such as the HYDRA microdispenser (Robbins Scientific, Sunnyvale Calif., MICROLAB 2200 (Hamilton, Reno Nev.), and the DNA ENGINE thermal cycler (PTC200; MJ Research, Watertown Mass.). Machines used for sequencing include the ABI 3700, 377 or 373 DNA sequencing systems (Perkin-Elmer), the MEGABACE 1000 DNA sequencing system (Amersham Pharmacia Biotech), and the like. The sequences may be analyzed using a variety of algorithms which are well known in the art and described in Ausubel (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative regions flanking the nucleic acid molecules of interest. Prefinished sequences (incomplete assembled sequences) are inspected for identity using various algorithms or programs such as CONSED (Gordon (1998) Genome Res. 8:195–202) which are well known in the art. Contaminating sequences including vector or chimeric sequences or deleted sequences can be removed or restored, respectively, organizing the prefinished sequences into finished sequences.

Extension of a Nucleic Acid Sequence

The sequences of the invention may be extended using various PCR-based methods known in the art. For example, the XL-PCR kit (Perkin-Elmer), nested primers, and commercially available cDNA or genomic DNA libraries (Life Technologies; Clontech, Palo Alto Cailf., respectively) may be used to extend the nucleic acid sequence. For all PCR-based methods, primers may be designed using commercially available software, such as OLIGO 4.06 Primer Analysis software (National Biosciences, Plymouth Minn.) to be about 22 to 30 nucleotides in length, to have a GC content of about 50% or more, and to anneal to a target molecule at temperatures from about 55° C. to about 68° C. When extending a sequence to recover regulatory elements, it is preferable to use genomic, rather than cDNA libraries.

Use of The Mammalian Nucleic Acid Molecule

Hybridization

The mammalian nucleic acid molecule and fragments thereof can be used in hybridization technologies for various purposes. A probe may be designed or derived from unique regions such as the 5' regulatory region or from a conserved motif such as the lipocalin family signature and used in protocols to identify naturally occurring molecules encoding the mammalian protein, allelic variants, or related molecules. The probe may be DNA or RNA, is usually single stranded and should have at least 50% sequence identity to any of the nucleic acid sequences. Hybridization probes may be produced using oligolabeling, nick translation, end-labeling, or PCR amplification in the presence of labeled nucleotide. A vector containing the nucleic acid molecule or a fragment thereof may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleic acid sequences that contain some mismatches. Subsequent washes are performed at higher stringency with buffers such as 0.2×SSC with 0.1% SDS at either 45° C. (medium stringency) or 68°0 C. (high stringency). At high stringency, hybridization complexes will remain stable only where the nucleic acid molecules are completely complementary. In some membrane-based hybridizations, perferably 35% or most preferably 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application WO 95/251116; Shalon et al. (1995) PCT application WO 95/35505; Heller et al. (1997) Proc. Natl. Acad. Sci. 94:2150–2155; and Heller et al. (1997) U.S. Pat. No. 5,605, 662.)

Hybridization probes are also useful in mapping the naturally occurring genomic sequence. The probes may be hybridized to: 1) a particular chromosome, 2) a specific region of a chromosome, 3) artificial chromosome constructions such as human artificial chromosomes (HACs), yeast artificial chromosomes (YACs), bacterial artificial chromosomes (BACs), bacterial P1 constructions, or single chromosomes or 5) CDNA libraries made from any of these sources.

Expression

A multitude of nucleic acid molecules encoding the mammalian lipocalin family protein may be cloned into a vector and used to express the protein, or portions thereof, in host cells. The nucleic acid sequence can be engineered by such methods as DNA shuffling (Stemmer and Crameri (1996) U.S. Pat. No. 5,830,721 incorporated by reference herein) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, nucleic acid molecule, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Cailf.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian nucleic acid molecule is based on DNA—DNA or DNA—RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Bethesda, Md.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Cailf. pp. S1–S20). Automated synthesis may also be carried out on machines such as the ABI 431 A Peptide synthesizer (Perkin-Elmer). A protein or portion thereof may be substantially purified by preparative high performance liquid chromatography and its composition confirmed by amino acid analysis or by sequencing (Creighton (1984) *Proteins, Structures and Molecular Properties*, WH Freeman, New York N.Y.).

Preparation and Screening of Antibodies

Various hosts including goats, rabbits, rats, mice, humans, and others may be immunized by injection with mammalian lipocalin family protein or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et a. (1975) Nature 256:495–497; Kozbor et al. (1985) J. Immunol. Methods 81:31–42; Cote et al. (1983) Proc. Natl. Acad. Sci. 80:2026–2030; and Cole et al. (1984) Mol. Cell Biol. 62:109–120.)

Alternatively, techniques described for the production of single chain antibodies may be adapted, using methods known in the art, to produce epitope specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275≧1281.)

The mammalian lipocalin family protein or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP (Amersham Pharmacia Biotech) or amino acid such as $^{35}$S-methionine (USB, Cleveland Ohio). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The nucleic acid molecules, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Conditions, diseases or disorders associated with altered expression include acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves'disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

For example, the nucleic acid molecule or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology*, Wiley-lnterscience, New York N.Y.; and Pound, supra.)

Therapeutics

Chemical and structural similarity, e.g., in the context of sequences and motifs, exists between regions of the SEQ ID NO:2 and SEQ ID NO:11 and other lipocalin family proteins, human apolipoprotein D (g4502163) and rat retinol binding protein (g113824). In addition, gene expression is closely associated with digestive system and reproductive tissues and appears to play a role in conditions such as cell proliferative and immune disorders. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves'disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising a substantially purified mammalian protein in conjunction with a pharmaceutical carrier may be administered to a subject to treat or prevent a condition associated with altered expression or activity of the endogenous protein including, but not limited to, those provided above.

In a further embodiment, a ligand which modulates the activity of the mammalian protein may be administered to a subject to treat or prevent a condition associated with altered lifespan, expression, or activity of the protein including, but not limited to, those listed above. In one aspect, an antibody which specifically binds the mammalian protein may be used as a targeting or delivery mechanism for bringing a pharmaceutical agent to cells or tissue which express the mammalian protein.

In an additional embodiment, a vector capable of expressing the mammalian protein or a portion or derivative thereof may be administered to a subject to treat or prevent a condition associated with altered lifespan, expression, or activity of protein including, but not limited to, those described above.

In a still further embodiment, a vector expressing the complement of the nucleic acid molecule or fragments thereof may be administered to a subject to treat or prevent a condition associated with altered lifespan, expression, or activity of the protein including, but not limited to, those described above.

Any of the nucleic acid molecules, complementary molecules and fragments thereof, proteins or portions thereof, vectors delivering these nucleic acid molecules or proteins, and their ligands may be administered in combination with other therapeutic agents. Selection of the agents for use in combination therapy may be made by one of ordinary skill in the art according to conventional pharmaceutical principles. A combination of therapeutic agents may act synergistically to effect prevention or treatment of a particular condition at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the mammalian gene. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library of nucleic acid molecules or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening Assays

The nucleic acid molecule encoding the mammalian protein may be used to screen a library of molecules for specific binding affinity. The libraries may be DNA molecules, RNA molecules, PNAs, peptides, proteins such as transcription factors, enhancers, repressors, and other ligands which regulate the activity, replication, transcription, or translation of the nucleic acid molecule in the biological system. The assay involves combining the mammalian nucleic acid molecule or a fragment thereof with the library of molecules under conditions allowing specific binding, and detecting specific binding to identify at least one molecule which specifically binds the nucleic acid molecule.

Similarly the mammalian protein or a portion thereof may be used to screen libraries of molecules in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs, or any other ligand, which specifically binds the protein. One method for high throughput screening using very small assay volumes and very small amounts of test compound is described in U.S. Pat. No. 5,876,946, incorporated herein by reference, which screens large numbers of molecules for enzyme inhibition or receptor binding.

Purification of Ligand

The nucleic acid molecule or a fragment thereof may be used to purify a ligand from a sample. A method for using a mammalian nucleic acid molecule or a fragment thereof to purify a ligand would involve combining the nucleic acid molecule or a fragment thereof with a sample under conditions to allow specific binding, detecting specific binding, recovering the bound protein, and using an appropriate agent to separate the nucleic acid molecule from the purified ligand.

Similarly, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle which produces the number of organisms needed to satisfy statistical requirements.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. No. 4,736,866; U.S. Pat. No. 5,175,383; and U.S. Pat. No. 5,767,337; incorporated herein by reference). In some cases, the introduced gene may be activated at a specific time in a specific tissue type during fetal development or postnatally. Expression of the transgene is monitored by analysis of phenotype or tissue-specific mRNA expression, in transgenic animals before, during, and after being challenged with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene which disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Then transformed ES cells are selected under conditions, identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168:342–357; Wiles and Keller(1991) Development 111:259–267; and Klugetal. (1996)J. Clin. Invest. 98:216–224). Recent developments demonstrate that ES cells derived from human blastocysts may also be manipulated in vitro to differentiate into eight separate cell lineages, including endoderm, mesoderm, and ectodermal cell types (Thomson (1998) Science 282:1145–1147).

Knockout Analysis

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc. Natl. Acad. Sci. 95:11371–11376; Baudoin et al. (1998) Genes Dev. 12:1202–1216; and Zhuang et al. (1998) Mol. Cell Biol. 18:3340–3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulatta*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPS are the first choice test animal. In addition, NHPS and individual humans exhibit differential sensitivities to many drugs and toxins and can be classified as "extensive metabolizers" and "poor metabolizers" of these agents.

In additional embodiments, the nucleic acid molecules which encode the mammalian protein may be used in any molecular biology techniques that have yet to be developed, provided the new techniques rely on properties of nucleic acid molecules that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, the preparation of the human kidney cDNA library, KIDNNOT20, is described.

I Representative cDNA sequence preparation

The human kidney cDNA library KIDNNOT20 was constructed from tissue obtained from a 43-year-old Caucasian male during nephroureterectomy and unilateral left adrenalectomy. The frozen tissue was homogenized and lysed in TRIZOL reagent (1 g tissue/10 ml TRIZOL; Life Technologies), a monophasic solution of phenol and guanidine isothiocyanate, using a POLYTRON homogenizer (PT-3000; Brinkmann Instruments, Westbury N.Y.). Following homogenization, chloroform was added (1:5 v/v chloroform:homogenate), and the lysate was centrifuged. The aqueous layer was removed, and the RNA was precipitated with isopropanol. The RNA was resuspended in DEPC-treated water and digested with DNase I (Life Technologies) for 25 min at 37° C. The RNA was re-extracted with acid phenol-chloroform, pH 4.7, and precipitated using 0.3M sodium acetate and 2.5 volumes ethanol.

Messenger RNA (mRNA) was isolated using the OLIGOTEX kit (Qiagen, Valencia Cailf.) and used to construct the cDNA library. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRi adaptors, and digested with NotI (New England Biolabs, Beverly Mass.). The DNAs were fractionated on a SEPHAROSE CL-4B column (Amersham Pharmacia Biotech), and those DNAs exceeding 400 bp were ligated into the NotI and EcoRI sites of the pINCY 1 plasmid (Incyte Pharmaceuticals, Palo Alto Cailf.). The plasmid was transformed into competent DH5α cells (Life Technologies) or ELECTROMAX DH10B cells (Life Technologies).

Plasmid DNA was released from the cells and purified using the REAL Prep 96 plasmid kit Qiagen). The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using the MICROLAB 2200 system (Hamilton, Reno Nev.) in combination with the DNA ENGINE thermal cyclers (MJ Research) and sequenced by the method of Sanger, F. and A. R. Calcine (1975; J. Mol. Biol. 94:441–448) using an ABI PRISM 377 sequencing system (Perkin Elmer). Most of the isolates were sequenced according to standard ABI protocols and kits (Perkin Elmer) with solution volumes of 0.25x–1.0x concentrations. In the alternative, cDNAs were sequenced using solutions and dyes from Amersham Pharmacia Biotech.

II Identification, Extension, Assembly, and Analyses

The consensus sequence (SEQ ID NO:10) was assembled from Incyte clones (SEQ ID NOs:6–9) from the ZOOSEQ database (Incyte Pharmaceuticals) of rat cDNA sequences with homology to mouse NG20 (SEQ ID NO:12) and used to identify additional sequences in the LIFESEQ database (Incyte Pharmaceuticals) related to lipocalin family proteins. The first pass cDNAs, SEQ ID Nos:3–5, were assembled using Phrap to produce SEQ ID NO:1. Translation of SEQ ID NO:1 and 10 using MACDNASIS PRO software (Hitachi Software Engineering) elucidated the coding regions, SEQ ID NO:2 and 11. The nucleic acid and amino acid sequences were queried against databases such as the GenBank databases, SwissProt, BLOCKS, PRINTS, Prosite, and PFAM using BLAST. Motifs and HMM algorithms were used to perform functional analyses, and the antigenic index (Jameson-Wolf analysis) was determined using LASERGENE software (DNASTAR).

III Sequence Similarity

Sequence similarity was calculated as percent identity based on comparisons between at least two nucleic acid molecules or amino acid sequences using the clustal method of the MEGALIGN program (DNASTAR). The clustal method uses an algorithm which groups sequences into clusters by examining the distances between all pairs. After the clusters are aligned pairwise, they are realigned in groups. Percent similarity between two sequences, sequence A and sequence B, is calculated by dividing the length of sequence A, minus the number of gap residues in sequence A, minus the number of gap residues in sequence B, into the sum of the residue matches between sequence A and sequence B, times 0ne hundred. Gaps of very low or zero similarity between the two sequences are not included.

IV Northern Analysis

Northern analysis is a laboratory technique used to detect the presence of a transcript of a gene and involves the hybridization of a labeled probe to a membrane on which RNAs from a particular cell type or tissue have been bound.

Analogous computer techniques applying BLAST were used to search for identical or related molecules in nucleotide databases such as GenBank or LIFESEQ (Incyte Pharmaceuticals). Sequence-based analysis is much faster than membrane-based hybridization, and the sensitivity of the computer search can be modified to determine whether any particular match is categorized as exact or similar. The basis of the search is the product score which is defined as: (percent sequence identity x percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a percentage distribution of libraries in which the transcript encoding the mammalian protein occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries across all categories.

V Extension of Nucleic Acid Molecules

At least one of the nucleic acid molecules used to assemble SEQ ID NOs:1 and 10 was produced by extension of an Incyte cDNA clone using oligonucleotide primers. One primer was synthesized to initiate 5' extension of the known fragment, and the other, to initiate 3' extension. The initial primers were designed using OLIGO 4.06 software (National Biosciences) to be about 22 to 30 nucleotides in length, to have a GC content of about 50%, and to anneal to the target sequence at temperatures of about 55° C. to about 68° C. Any fragment which would result in hairpin structures and primer-primer dimerizations was avoided. Selected human cDNA libraries were used to extend the molecule. If more than one extension is needed, additional or nested sets of primers are designed.

High fidelity amplification was obtained by performing PCR in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, parameters for the primer pair, T7 and SK+ (Stratagene), were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v); Molecular Probes) dissolved in 1X TE and 0.5 μl of undiluted PCR product into each well of an opaque fluorimeter plate (Corning Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA. A 5, μl to 10 μl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments were separated on about 0.6–0.8% agarose gels, fragments were excised as visualized under UV light, and agar removed/digested with AGARACE (Promega). Extended fragments were religated using T4 DNA ligase (New England Biolabs, Beverly Mass.) into pUC 18 vector (Amersham Pharmacia Biotech), treated with Pfu DNA polymerase (Stratagene) to fill-in restriction site overhangs, and transformed into competent *E. coli* cells. Transformed cells were selected on antibiotic-containing media, and individual colonies were picked and cultured overnight at 37° C. in 384-well plates in LB/2× carbenicillin liquid media.

The cells were lysed, and DNA was amplified using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleic acid molecule of SEQ ID NOs:1 or 10 is used to obtain regulatory sequences using the procedure above, oligonucleotides designed for outward extension, and a genomic DNA library.

VI Labeling of Probes and Hybridization Analyses

Nucleic acids are isolated from a biological source and applied to a substrate for standard hybridization protocols by one of the following methods. A mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20× saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 beads (Amersham Pharmacia Biotech). Purified target nucleic acids are robotically arrayed onto a glass microscope slide (Corning Science Products, Corning N.Y.). The slide is previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probes are made from mRNA templates. Five micrograms of mRNA is mixed with 1 μg random primer (Life Technologies), incubated at 70° C. for 10 minutes, and lyophilized. The lyophilized sample is resuspended in 50 μl of 1× first strand buffer (cDNA Synthesis systems; Life Technologies) containing a dNTP mix, [α-$^{32}$P]dCTP, dithiothreitol, and MMLV reverse transcriptase (Stratagene), and incubated at 42° C. for 1–2 hours. After incubation, the probe is diluted with 42 μl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 MicroColumn (Amersham Pharmacia Biotech). Probes can be labeled with fluorescent markers, Cy3-dCTP or Cy5-dCTP (Amersham Pharmacia Biotech), in place of the radionucleotide, [$^{32}$P] dCTP.

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probes. After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the substrate is examined by confocal laser microscopy, and images are collected and analyzed using GEMTOOLS gene expression analysis software (Incyte Pharmaceuticals).

VII Complementary Nucleic Acid Molecules

Molecules complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or their derivatives (PNAs). Oligonucleotides are designed using OLIGO 4.06 software (National Biosciences) and SEQ ID NOs:1 and 3–10. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

VIII Expression of the Mammalian Protein

Expression and purification of the mammalian protein are achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the irp-lac (tac) hybrid promoter and the T5 or T7 bacteriophage promoter in conjunction with the lac operator regulatory element. Recombinant vectors are transformed into bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera fruyiperda* (St9) insect cells with recombinant baculovirus, *Autooraphica californica* nuclear polyhedrosis virus. The polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., glutathione S-transferase (GST) or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity (Amersham Pharmacia Biotech). Following purification, the GST moiety can be proteolytically cleaved from the mammalian protein at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (supra, unit 16). Purified mammalian protein obtained by these methods can be used directly in the following activity assay.

IX Functional Assays

Protein function is assessed by expressing the sequences encoding LCFP at physiologically elevated levels in mammalian cell culture. The nucleic acid molecule is subcloned into PCMV SPORT vector (Life Technologies), which contains the strong cytomegalovirus promoter, and 5–10 μg of the vector is transformed into a endothelial or hematopoietic human cell line using transformation methods well known in the art. An additional 1–2 μg of a plasmid containing sequence encoding CD64-GFP (Clontech) is co-transformed to provide a fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells are separated using magnetic beads coated with either human IgG or antibody against CD64 (DYNAL, Lake Success N.Y.). mRNA is purified from the cells and analyzed by hybridization techniques.

X Production of LCFP Specific Antibodies

LCFP is purified using polyacrylamide gel electrophoresis and used to immunize mice or rabbits. Antibodies are produced using the protocols below. Alternatively, the amino acid sequence of LCFP is analyzed using LASERGENE software (DNASTAR) to determine regions of high immunogenicity. An immunogenic epitope, usually found near the C-terminus or in a hydrophilic region is selected, synthesized, and used to raise antibodies. Typically, epitopes of about 15 residues in length are produced using an ABI 431 A Peptide synthesizer (Perkin-Elmer) using Fmoc-chemistry and coupled to KLH (Sigma-Aldrich) by reaction with N-maleimidobenzoyl-N-hydroxysuccinimide ester to increase immunogenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XI Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersham Pharmacia Biotech). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XII Screening Molecules for Specific Binding with the Nucleic Acid Molecule or Protein The nucleic acid molecule, or fragments thereof, or the protein, or portions thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Libraries of candidate molecules previously arranged on a substrate are incubated in the presence of labeled nucleic acid molecule or protein. After incubation under conditions for either a nucleic acid or amino acid sequence, the substrate is washed, and any position on the substrate retaining label, which indicates specific binding or complex formation, is assayed, and the binding molecule is identified. Data obtained using different concentrations of the nucleic acid or protein are used to calculate affinity between the labeled nucleic acid or protein and the bound molecule.

XIII Demonstration of Protein Activity

LCFP, or biologically active fragments thereof, are labeled with $^{251}$I Bolton-Hunter reagent (Bolton et al. (1973) Biochem. J. 133:529–539). Candidate ligand molecules previously arrayed in the wells of a multi-well plate are incubated with the labeled LCFP, washed, and any wells with labeled LCFP complex are assayed. Data obtained using different concentrations of LCFP are used to calculate values for the number, affinity, and association of LCFP with the candidate ligand molecules.

Table 1 compares Incyte rat and human nucleic acid molecules including their length, biological source, region of overlap with SEQ ID NO:1, and percent identity with SEQ ID NO:1 (MEGALIGN program, DNASTAR).

TABLE 1

| Nucleic Acid SEQ ID NO: | Incyte Clone Number | Nucleotide Length | Source | Library | Coverage | Percent Identity |
|---|---|---|---|---|---|---|
| 3 | 4069566H1 | 289 | Homo sapiens | KIDNNOT26 | 1–289 | n/a |
| 4 | 4419443H1 | 260 | Homo sapiens | LIVRDIT02 | 258–518 | n/a |
| 5 | 2865127H1 | 303 | Homo sapiens | KIDNNOT20 | 457–759 | n/a |
| 6 | 701318182H1 | 249 | Rattus norvegicus | RALITXT06 | 1–218 | 57.0 |
| 7 | 700046753F1 | 265 | Rattus norvegicus | RALINOT01 | 34–289 | 74.3 |

TABLE 1-continued

| Nucleic Acid SEQ ID NO: | Incyte Clone Number | Nucleotide Length | Source | Library | Coverage | Percent Identity |
|---|---|---|---|---|---|---|
| 8 | 701427716T1 | 587 | *Rattus norvegicus* | RALINOT02 | 125–705 | 74.3 |
| 9 | 700608183H1 | 236 | *Rattus norvegicus* | RALINOH01 | 505–748 | 79.2 |

What is claimed is:

1. A substantially purified mammalian nucleic acid molecule encoding a lipocalin family protein of SEQ ID NO:2 or SEQ ID NO:11.

2. An isolated and purified mammalian nucleic acid molecule comprising the nucleic acid sequence selected from the group consisting of SEQ ID NO:1 and SEQ ID NO:10.

3. A fragment of the mammalian nucleic acid molecule of claim 1 selected from the group consisting of SEQ ID NOs:3–9.

4. The complement of the nucleic acid molecule of claim 1.

5. The complement of the fragment of claim 3.

6. An expression vector comprising the mammalian nucleic acid molecule of claim 1.

7. A host cell containing the expression vector of claim 7.

8. A method for producing a protein, the method comprising the steps of:

(a) culturing the host cell of claim 7 under conditions for the expression of the protein; and (b) recovering the protein from the host cell culture.

9. A method for detecting a mammalian nucleic acid molecule in a sample, the method comprising the steps of:

(a) hybridizing the nucleic acid molecule of claim 4 to at least one nucleic acid molecule in the sample, thereby forming a hybridization complex; and (b) detecting the hybridization complex, wherein the presence of the hybridization complex indicates the presence of the mammalian nucleic acid molecule in the sample.

10. The method of claim 9 further comprising amplifying the nucleic acid molecules of the sample prior to hybridization.

11. A method of using a mammalian nucleic acid molecule to screen a library of molecules to identify at least one ligand which specifically binds the nucleic acid molecule, the method comprising:

(a) providing a library of molecules, (b) combining the nucleic acid molecule of claim 1 with a library of molecules under conditions to allow specific binding, and (c) detecting specific binding, thereby identifying a ligand which specifically binds the nucleic acid molecule.

12. The method of claim 11 wherein the library is selected from the group consisting of DNA molecules, RNA molecules, PNAs, peptides, and proteins.

13. A method of using a mammalian nucleic acid molecule or a fragment thereof to purify a ligand which specifically binds the nucleic acid molecule from a sample, the method comprising:

a) combining the mammalian nucleic acid molecule of claim 1 with a sample under conditions to allow specific binding, and b) detecting specific binding between the nucleic acid molecule and a ligand, c) recovering the bound nucleic acid molecule, and d) separating the nucleic acid molecule from the ligand, thereby obtaining purified ligand.

\* \* \* \* \*

SEQUENCE LISTING

<160> NUMBER OF SEQ ID NOS: 14

<210> SEQ ID NO 1
<211> LENGTH: 757
<212> TYPE: DNA
<213> ORGANISM: Homo sapiens
<220> FEATURE:
<221> NAME/KEY: unsure
<222> LOCATION: 689, 752, 754
<223> OTHER INFORMATION: a or g or c or t, unknown, or other
<220> FEATURE:
<221> NAME/KEY:
<223> OTHER INFORMATION: 2865127
<300> PUBLICATION INFORMATION:

<400> SEQUENCE: 1

```
gcagccagta ggggagagag cagttaaggc acacagagca ccagctccct cctgcctgaa      60
gatgttccac caaatttggg cagctctgct ctacttctat ggtattatcc ttaactccat     120
ctaccagtgc cctgagcaca gtcaactgac aactctgggc gtggatggga aggagttccc     180
agaggtccac ttgggccagt ggtactttat cgcaggggca gctcccacca aggaggagtt     240
ggcaactttt gaccctgtgg acaacattgt cttcaatatg gctgctggct ctgccccgat     300
gcagctccac cttcgtgcta ccatccgcat gaaagatggg ctctgtgtgc cccggaaatg     360
gatctaccac ctgactgaag ggagcacaga tctcagaact gaaggccgcc ctgacatgaa     420
gactgagctc ttttccagct catgcccagg tggaatcatg ctgaatgaga caggccaggg     480
ttaccagcgc tttctcctct acaatcgctc accacatcct cccgaaaagt gtgtggagga     540
attcaagtcc ctgacttcct gcctggactc caaagccttc ttattgactc ctaggaatca     600
agaggcctgt gagctgtcca ataactgacc tgtaacttca tctaagtccc cagatgggta     660
caatgggagc tgagttgttg gagggagang ctggagactt ccagctccag ctcccactca     720
agataataaa gataattttt caatcctcaa ananaaa                              757
```

<210> SEQ ID NO 2
<211> LENGTH: 188
<212> TYPE: PRT
<213> ORGANISM: Homo sapiens
<220> FEATURE:
<221> NAME/KEY:
<223> OTHER INFORMATION: 2865127
<300> PUBLICATION INFORMATION:

<400> SEQUENCE: 2

```
Met Phe His Gln Ile Trp Ala Ala Leu Leu Tyr Phe Tyr Gly Ile
  1               5                  10                  15

Ile Leu Asn Ser Ile Tyr Gln Cys Pro Glu His Ser Gln Leu Thr
                 20                  25                  30

Thr Leu Gly Val Asp Gly Lys Glu Phe Pro Glu Val His Leu Gly
                 35                  40                  45

Gln Trp Tyr Phe Ile Ala Gly Ala Ala Pro Thr Lys Glu Glu Leu
```

-continued

```
                 50                  55                  60
Ala Thr Phe Asp Pro Val Asp Asn Ile Val Phe Asn Met Ala Ala
                 65                  70                  75
Gly Ser Ala Pro Met Gln Leu His Leu Arg Ala Thr Ile Arg Met
                 80                  85                  90
Lys Asp Gly Leu Cys Val Pro Arg Lys Trp Ile Tyr His Leu Thr
                 95                 100                 105
Glu Gly Ser Thr Asp Leu Arg Thr Glu Gly Arg Pro Asp Met Lys
                110                 115                 120
Thr Glu Leu Phe Ser Ser Cys Pro Gly Ile Met Leu Asn
                125                 130                 135
Glu Thr Gly Gln Gly Tyr Gln Arg Phe Leu Leu Tyr Asn Arg Ser
                140                 145                 150
Pro His Pro Pro Glu Lys Cys Val Glu Phe Lys Ser Leu Thr
                155                 160                 165
Ser Cys Leu Asp Ser Lys Ala Phe Leu Leu Thr Pro Arg Asn Gln
                170                 175                 180
Glu Ala Cys Glu Leu Ser Asn Asn
                185
```

```
<210> SEQ ID NO 3
<211> LENGTH: 289
<212> TYPE: DNA
<213> ORGANISM: Homo sapiens
<220> FEATURE:
<221> NAME/KEY:
<223> OTHER INFORMATION: 4069566H1
<300> PUBLICATION INFORMATION:

<400> SEQUENCE: 3
gcagccagta ggggagagag cagttaaggc acacagagca ccagctccct cctgcctgaa      60
gatgttccac caaatttggg cagctctgct ctacttctat ggtattatcc ttaactccat     120
ctaccagtgc cctgagcaca gtcaactgac aactctgggc gtggatggga aggagttccc     180
agaggtccac ttgggccagt ggtactttat cgcagggca gctcccacca aggaggagtt     240
ggcaactttt gaccctgtgg acaacattgt cttcaatatg ctgctggc                  289

<210> SEQ ID NO 4
<211> LENGTH: 260
<212> TYPE: DNA
<213> ORGANISM: Homo sapiens
<220> FEATURE:
<221> NAME/KEY:
<223> OTHER INFORMATION: 4419443H1
<300> PUBLICATION INFORMATION:

<400> SEQUENCE: 4
gggacaacat tgtcttcaat atgctgctg gctctgcccc gatgcagctc cacctttcgt      60
gctaccatcc gcatgaaaga tgggctctgt gtgccccgga aatggatcta ccacctgact    120
gaagggagca cagatctcag aactgaaggc cgccctgaca tgaagactga gctcttttcc    180
agctcatgcc caggtggaat catgctgaat gagacaggcc agggttacca gcgctttctc    240
ctctacaatc gctcaccaca                                                260

<210> SEQ ID NO 5
<211> LENGTH: 303
<212> TYPE: DNA
<213> ORGANISM: Homo sapiens
<220> FEATURE:
```

```
<221> NAME/KEY: unsure
<222> LOCATION: 14, 26, 235, 298, 300
<223> OTHER INFORMATION: a or g or c or t, unknown, or other
<220> FEATURE:
<221> NAME/KEY:
<223> OTHER INFORMATION: 2865127H1
<300> PUBLICATION INFORMATION:

<400> SEQUENCE: 5
tcatgctgaa tganacaggc cagggnttac cagcgctttc tcctctacaa tcgctcacca      60
catcctcccg aaaagtgtgt ggaggaattc aagtccctga cttcctgcct ggactccaaa    120
gccttcttat tgactcctag gaatcaagag gcctgtgagc tgtccaataa ctgacctgta    180
acttcatcta gtccccaga tgggtacaat gggagctgag ttgttggagg gagangctgg     240
agacttccag ctccagctcc cactcaagat aataaagata attttcaat cctcaaanan     300 aaa                                                                  303

<210> SEQ ID NO 6
<211> LENGTH: 249
<212> TYPE: DNA
<213> ORGANISM: Rattus norvegicus
<220> FEATURE:
<221> NAME/KEY:
<223> OTHER INFORMATION: 701318182H1
<300> PUBLICATION INFORMATION:

<400> SEQUENCE: 6
gggggctgga ggcagagcag actgggcatg ccagcagaga acagttaagg tagaggtccc     60
cagaaccgca cagcgccagg tctcctccca agatgttcca ccaagtctgg gcagcgctgc   120
tctatctcta cggccttctc tttaactcca tgaatcagtg ccctgagcac agtcaactaa    180
cgacgctggg aatggacgac aaagagaccc cagagcccca cctgggcctg tggtacttta    240
tcgctggag                                                             249

<210> SEQ ID NO 7
<211> LENGTH: 265
<212> TYPE: DNA
<213> ORGANISM: Rattus norvegicus
<220> FEATURE:
<221> NAME/KEY:
<223> OTHER INFORMATION: 700046753F1
<300> PUBLICATION INFORMATION:

<400> SEQUENCE: 7
gtccccagaa ccgcacagcg ccaggtctcc tcccaagatg ttccaccaag tctgggcagc     60
gctgctctat ctctacggcc ttctctttaa ctccatgaat cagtgccctg agcacagtca   120
actaacgacg ctgggaatgg acgacaaaga gaccccagag ccccacctgg gcctgtggta   180
ctttatcgct ggagcggctc ccaccatgga agagttggca acttttgacc aggtagacaa   240
tattgtcttc aacatggccg ccggc                                          265

<210> SEQ ID NO 8
<211> LENGTH: 587
<212> TYPE: DNA
<213> ORGANISM: Rattus norvegicus
<220> FEATURE:
<221> NAME/KEY: unsure
<222> LOCATION: 398
<223> OTHER INFORMATION: a or g or c or t, unknown, or other
<220> FEATURE:
<221> NAME/KEY:
<223> OTHER INFORMATION: 701427716T1
<300> PUBLICATION INFORMATION:
```

<400> SEQUENCE: 8

```
gcgggagtcg ctggcttctc ccctcagagc tcagctccta tcgtgcctgt ccaggacaca       60
ggtggagtca cgggtcactt gctggacagt gggcaggcct cttgattcct gggagtcact      120
aaaaaggctt tgaagtccaa gcaggatgtc agagactgga attcctccac acactcctct      180
ggagggtgtg gcgatcggtt gtagaggagg aaacgctggt acccctgccc cgtctctttc      240
agcatgattc ctcctgggca tgagatggag aagaggtctg ttttcatgtc tgggcgccct      300
tcagttctga gttccgtgtt tcctttccct tcagtcaagt ggtacgtcca tttccggggc      360
acacagaccc cgttttttcgt gcgaatggta gcgcgaantg gaagctgcct tggggcagag      420
ccggcggcca tgttgaagac aatattgtct acctggtcaa aagttgccaa ctcttccatg      480
gtgggagccg cttccagcga taaagtacca caggcccagg tggggctctg ggggtctctt      540
tgtcgtccat tcccagcgt cgttagttga ctgtgctcag ggcacta                     587
```

<210> SEQ ID NO 9
<211> LENGTH: 236
<212> TYPE: DNA
<213> ORGANISM: Rattus norvegicus
<220> FEATURE:
<221> NAME/KEY: unsure
<222> LOCATION: 7, 9, 34, 98
<223> OTHER INFORMATION: a or g or c or t, unknown, or other
<220> FEATURE:
<221> NAME/KEY:
<223> OTHER INFORMATION: 700608183H1
<300> PUBLICATION INFORMATION:

<400> SEQUENCE: 9

```
ccgatcncna caccctccag aggagtgtgt ggangaattc cagtctctga catcctgctt       60
ggacttcaaa gccttttttag tgactcccag gaatcaanag gcctgcccac tgtccagcaa      120
gtgacccgtg actccacctg tgtcctggac aggcacgata ggagctgagc tctgagggga      180
gaagccagcg actcccgctc cctctcatgg atagtaaaga tgaattgtca atcctc           236
```

<210> SEQ ID NO 10
<211> LENGTH: 777
<212> TYPE: DNA
<213> ORGANISM: Rattus norvegicus
<220> FEATURE:
<221> NAME/KEY:
<223> OTHER INFORMATION: 700046753
<300> PUBLICATION INFORMATION:

<400> SEQUENCE: 10

```
gggggctgga ggcagagcag actgggcatg ccagcagaga acagttaagg tagaggtccc       60
cagaaccgca cagcgccagg tctcctccca agatgttcca ccaagtctgg gcagcgctgc      120
tctatctcta cggccttctc tttaactcca tgaatcagtg ccctgagcac agtcaactaa      180
cgacgctggg aatggacgac aaagagaccc cagagcccca cctgggcctg tggtacttta      240
tcgctggagc ggctcccacc atggaagagt tggcaacttt tgaccaggta gacaatattg      300
tcttcaacat ggccgccggc tctgccccaa ggcagctcca gcttcgcgct accattcgca      360
cgaaaaacgg ggtctgtgtg ccccggaaat ggacgtacca cttgactgaa gggaaaggaa      420
acacggaact cagaactgaa gggcgcccag acatgaaaac agacctcttc tccatctcat      480
gcccaggagg aatcatgctg aaagagacgg ggcagggta ccagcgtttc ctcctctaca      540
accgatcgcc acaccctcca gaggagtgtg tggaggaatt ccagtctctg acatcctgct      600
```

```
tggacttcaa agccttttta gtgactccca ggaatcaaga ggcctgccca ctgtccagca    660
agtgacccgt gactccacct gtgtcctgga caggcacgat aggagctgag ctctgagggg    720
agaagccagc gactcccgct ccctctcatg gataataaag atgaattgtc aatcctc       777
```

```
<210> SEQ ID NO 11
<211> LENGTH: 190
<212> TYPE: PRT
<213> ORGANISM: Rattus norvegicus
<220> FEATURE:
<221> NAME/KEY:
<223> OTHER INFORMATION: 700046753
<300> PUBLICATION INFORMATION:

<400> SEQUENCE: 11

Met Phe His Gln Val Trp Ala Ala Leu Leu Tyr Leu Tyr Gly Leu
  1               5                  10                  15

Leu Phe Asn Ser Met Asn Gln Cys Pro Glu His Ser Gln Leu Thr
                 20                  25                  30

Thr Leu Gly Met Asp Asp Lys Glu Thr Pro Glu Pro His Leu Gly
                 35                  40                  45

Leu Trp Tyr Phe Ile Ala Gly Ala Ala Pro Thr Met Glu Glu Leu
                 50                  55                  60

Ala Thr Phe Asp Gln Val Asp Asn Ile Val Phe Asn Met Ala Ala
                 65                  70                  75

Gly Ser Ala Pro Arg Gln Leu Gln Leu Arg Ala Thr Ile Arg Thr
                 80                  85                  90

Lys Asn Gly Val Cys Val Pro Arg Lys Trp Thr Tyr His Leu Thr
                 95                 100                 105

Glu Gly Lys Gly Asn Thr Glu Leu Arg Thr Gly Arg Pro Asp
                110                 115                 120

Met Lys Thr Asp Leu Phe Ser Ile Ser Cys Pro Gly Gly Ile Met
                125                 130                 135

Leu Lys Glu Thr Gly Gln Gly Tyr Gln Arg Phe Leu Leu Tyr Asn
                140                 145                 150

Arg Ser Pro His Pro Pro Glu Cys Val Glu Glu Phe Gln Ser
                155                 160                 165

Leu Thr Ser Cys Leu Asp Phe Lys Ala Phe Leu Val Thr Pro Arg
                170                 175                 180

Asn Gln Glu Ala Cys Pro Leu Ser Ser Lys
                185                 190
```

```
<210> SEQ ID NO 12
<211> LENGTH: 190
<212> TYPE: PRT
<213> ORGANISM: Mus musculus
<220> FEATURE:
<221> NAME/KEY:
<223> OTHER INFORMATION: g3941735
<300> PUBLICATION INFORMATION:

<400> SEQUENCE: 12

Met  Phe His Gln Val Trp Ala Ala Leu Leu Ser Leu Tyr Gly Leu
  1               5                  10                  15

Leu Phe Asn Ser Met Asn Gln Cys Pro Glu His Ser Gln Leu Thr
                 20                  25                  30

Ala Leu Gly Met Asp Asp Thr Glu Thr Pro Glu Pro His Leu Gly
                 35                  40                  45

Leu Trp Tyr Phe Ile Ala Gly Ala Ala Ser Thr Thr Glu Glu Leu
```

```
                     50                  55                  60
Ala Thr Phe Asp Pro Val Asp Asn Ile Val Phe Asn Met Ala Ala
                 65                  70                  75

Gly Ser Ala Pro Arg Gln Leu Gln Leu Arg Ala Thr Ile Arg Thr
                 80                  85                  90

Lys Ser Gly Val Cys Val Pro Arg Lys Trp Thr Tyr Arg Leu Thr
                 95                 100                 105

Glu Gly Lys Gly Asn Met Glu Leu Arg Thr Glu Gly Arg Pro Asp
                110                 115                 120

Met Lys Thr Asp Leu Phe Ser Ser Cys Pro Gly Gly Ile Met
                125                 130                 135

Leu Lys Glu Thr Gly Gln Gly Tyr Gln Arg Phe Leu Leu Tyr Asn
                140                 145                 150

Arg Ser Pro His Pro Pro Glu Lys Cys Val Glu Glu Phe Gln Ser
                155                 160                 165

Leu Thr Ser Cys Leu Asp Phe Lys Ala Phe Leu Val Thr Pro Arg
                170                 175                 180

Asn Gln Glu Ala Cys Pro Leu Ser Ser Lys
                185                 190

<210> SEQ ID NO 13
<211> LENGTH: 189
<212> TYPE: PRT
<213> ORGANISM: Homo sapiens
<220> FEATURE:
<221> NAME/KEY:
<223> OTHER INFORMATION: g4502163
<300> PUBLICATION INFORMATION:

<400> SEQUENCE: 13

Met Val Met Leu Leu Leu Leu Ser Ala Leu Ala Gly Leu Phe
 1               5                  10                  15

Gly Ala Ala Glu Gly Gln Ala Phe His Leu Gly Lys Cys Pro Asn
                 20                  25                  30

Pro Pro Val Gln Glu Asn Phe Asp Val Asn Lys Tyr Leu Gly Arg
                 35                  40                  45

Trp Tyr Glu Ile Glu Lys Ile Pro Thr Thr Phe Glu Asn Gly Arg
                 50                  55                  60

Cys Ile Gln Ala Asn Tyr Ser Leu Met Glu Asn Gly Lys Ile Lys
                 65                  70                  75

Val Leu Asn Gln Glu Leu Arg Ala Asp Gly Thr Val Asn Gln Ile
                 80                  85                  90

Glu Gly Glu Ala Thr Pro Val Asn Leu Thr Glu Pro Ala Lys Leu
                 95                 100                 105

Glu Val Lys Phe Ser Trp Phe Met Pro Ser Ala Pro Tyr Trp Ile
                110                 115                 120

Leu Ala Thr Asp Tyr Glu Asn Tyr Ala Leu Val Tyr Ser Cys Thr
                125                 130                 135

Cys Ile Ile Gln Leu Phe His Val Asp Phe Ala Trp Ile Leu Ala
                140                 145                 150

Arg Asn Pro Asn Leu Pro Pro Glu Thr Val Asp Ser Leu Lys Asn
                155                 160                 165

Ile Leu Thr Ser Asn Asn Ile Asp Val Lys Lys Met Thr Val Thr
                170                 175                 180

Asp Gln Val Asn Cys Pro Lys Leu Ser
                185
```

```
<210> SEQ ID NO 14
<211> LENGTH: 188
<212> TYPE: PRT
<213> ORGANISM: Rattus norvegicus
<220> FEATURE:
<221> NAME/KEY:
<223> OTHER INFORMATION: gl13824
<300> PUBLICATION INFORMATION:

<400> SEQUENCE: 14

Met Glu Asn Ile Met Pro Phe Ala Leu Leu Gly Leu Cys Val Gly
 1               5                  10                  15

Leu Ala Ala Gly Thr Glu Gly Ala Val Val Lys Asp Phe Asp Ile
                20                  25                  30

Ser Lys Phe Leu Gly Phe Trp Tyr Glu Ile Ala Phe Ala Ser Lys
                35                  40                  45

Met Gly Thr Pro Gly Leu Ala His Lys Glu Glu Lys Met Gly Ala
                50                  55                  60

Met Val Val Glu Leu Lys Glu Asn Leu Leu Ala Leu Thr Thr Thr
                65                  70                  75

Tyr Tyr Ser Glu Asp His Cys Val Leu Glu Lys Val Thr Ala Thr
                80                  85                  90

Glu Gly Asp Gly Pro Ala Lys Phe Gln Val Thr Arg Leu Ser Gly
                95                 100                 105

Lys Lys Glu Val Val Val Glu Ala Thr Asp Tyr Leu Thr Tyr Ala
               110                 115                 120

Ile Ile Asp Ile Thr Ser Leu Val Ala Gly Ala Val His Arg Thr
               125                 130                 135

Met Lys Leu Tyr Ser Arg Ser Leu Asp Asp Asn Gly Glu Ala Leu
               140                 145                 150

Tyr Asn Phe Arg Lys Ile Thr Ser Asp His Gly Phe Ser Glu Thr
               155                 160                 165

Asp Leu Tyr Ile Leu Lys His Asp Leu Thr Cys Val Lys Val Leu
               170                 175                 180

Gln Ser Ala Ala Glu Ser Arg Pro
               185
```